United States Patent [19]

Coburn et al.

[11] Patent Number: 4,939,132

[45] Date of Patent: Jul. 3, 1990

[54] NOVEL 5-ALKYLSULFONYLSALICYLANILIDES AND MICROBIOCIDAL COMPOSITIONS FOR CONTROLLING THE GROWTH OF MICROORGANISMS

[75] Inventors: Robert A. Coburn, Williamsville; Richard T. Evans, East Amherst; Robert J. Genco, Buffalo, all of N.Y.; Michael T. Clark, Worthington, Ohio

[73] Assignee: The Research Foundation of State University of New York, Albany, N.Y.

[21] Appl. No.: 723,080

[22] Filed: Apr. 15, 1985

[51] Int. Cl.$^5$ .................. C07C 147/11; A61K 31/60; A61K 31/165

[52] U.S. Cl. ........................ 514/166; 424/52; 424/54; 424/55; 564/162; 564/166; 564/169; 514/618

[58] Field of Search ............... 514/166, 618; 564/162, 564/169, 166; 424/52, 55, 54

[56] References Cited

U.S. PATENT DOCUMENTS

| | | | |
|---|---|---|---|
| 3,027,301 | 1/1962 | Freedman et al. | 167/65 |
| 3,113,067 | 3/1963 | Strufe et al. | 167/30 |
| 3,317,583 | 6/1967 | Hsi | 260/465 |
| 3,377,238 | 11/1968 | Ehrenford | 167/30 |
| 3,681,458 | 8/1972 | Ruschig et al. | 260/559 S |
| 3,888,980 | 5/1975 | Meek | 424/230 |
| 3,917,617 | 10/1975 | Razdan et al. | 260/293.77 |
| 3,929,879 | 12/1975 | Taborsky | 260/559 S |
| 3,976,668 | 8/1976 | Richter | 564/162 X |
| 3,989,826 | 10/1976 | Forsyth et al. | 424/230 |
| 4,008,274 | 4/1977 | Sawatari et al. | 260/559 S |
| 4,025,647 | 5/1977 | Eakin et al. | 424/304 |
| 4,079,148 | 3/1978 | Oeckl et al. | 514/618 X |
| 4,200,632 | 4/1980 | Nakagawa et al. | 424/230 |
| 4,287,191 | 9/1981 | Coburn et al. | 424/230 |
| 4,358,443 | 11/1982 | Coburn et al. | 424/230 |

FOREIGN PATENT DOCUMENTS

| | | |
|---|---|---|
| 1094578 | 2/1955 | France . |
| 1299134 | 6/1962 | France . |
| 157334 | 3/1975 | Japan . |
| 35127 | 4/1975 | Japan . |
| 129738 | 10/1975 | Japan . |
| 100039 | 10/1976 | Japan . |
| 125737 | 12/1976 | Japan . |
| 85138 | 4/1977 | Japan . |
| 1817 | 1/1978 | Japan . |
| 2219 | 1/1979 | Japan . |
| 946029 | 1/1964 | United Kingdom . |
| 1229669 | 9/1971 | United Kingdom . |

OTHER PUBLICATIONS

Chem. Abs. 776, 14767(g) (1972) Rotmistrov et al.
Chem. Abs. 82, 97859(r) (1985) Umezawa et al.
Chem. Abs. 84 58970(s) (1976) Umezawa et al.
Chem. Abs. 84 55311(s) (1976) Sawatari et al.
Chem. Abs. 88 69825(s) (1978) Stecker.
Disinfection, Sterilization & Preservation 2nd, pp. 282-291.

*Primary Examiner*—Carolyn S. Elmore
*Attorney, Agent, or Firm*—Michael L. Dunn

[57] ABSTRACT

This invention relates to new 5-alkylsulfonylsalicylanilides and methods for their use. More particularly, the invention relates to compounds of the formula:

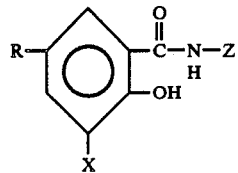

Wherein Z is a substituted or unsubstituted phenyl ring of from 6 to 30 carbon atoms including substituents, R is a substituted or unsubstituted alkylsulfonyl group of from 1 to 20 carbon atoms including substitutents; and X is a radical selected from the group consisting of —CN, —NO$_2$, —H, halogen, lower alkyl or lower haloalkyl.

The above compounds and compositions containing them are effective antiseptics against a wide range of microorganisms, especially bacteria, and are surprisingly highly effective against microorganisms, particularly *S. mutans*, prevalent in dental plaque.

26 Claims, No Drawings

NOVEL 5-ALKYLSULFONYLSALICYLANILIDES AND MICROBIOCIDAL COMPOSITIONS FOR CONTROLLING THE GROWTH OF MICROORGANISMS

This invention relates to new compounds and methods for killing or controlling the growth of microorganisms and more particularly relates to certain substituted sulfonyl-salicylamide compounds having antimicrobial activity which are particularly useful in controlling the growth of microorganisms related to dental plaques and associated diseases.

FIELD OF THE INVENTION

Historically, compositions and methods have been sought for killing and controlling the growth of microorganisms, particularly those related to disease. The compositions which have been discovered for this purpose have typically had one or more disadvantage. Generally, the compositions have not been effective against all undesirable microorganisms such as disease causing bacteria. Some of the prior art compositions have permitted certain microorganisms to develop an immunity or tolerance for the composition, while others have been more toxic to higher order organisms than desirable. Still others have caused allergic reactions in the host, or have been expensive and difficult to manufacture or purify.

These disadvantages have been particularly noticeable in compositions used to control the growth of bacteria related to dental plaque and associated diseases. Prior art compositions used for this purpose are either insufficiently effective, are too toxic or both. Toxic, as used herein, means that the composition causes damage to mammalian organisms, especially humans, which may use the composition to control the growth of an undesired microorganism. Damage may occur whether the composition is applied topically or otherwise.

Many compositions, formerly and even currently, in use as mammalian oral antiseptics contain large quantities of chlorine or bromine, often attached to a phenyl amine ring. In general such aromatic amine chlorinated and brominated compounds are to be avoided due to toxicity and even carcinogenicity, which has often been associated with such compounds. Furthermore, such compounds when used as oral antiseptics are usually not sufficiently effective at low concentrations to treat dental plaques and associated diseases.

Chlorhexidine is an example of a compound which contains chlorine attached to a phenyl amine ring which is or has been used as an oral antiseptic. Another compound which has been used as an antiseptic is tribromosalan, a brominated salicylanilide. This latter compound is an effective antiseptic but is not as effective as desired in killing or inhibiting the growth of plaque causing organisms at low concentrations. Examples of other compounds which are used as oral antiseptics and which contain chlorine or bromine are cetylpyridinium chloride and domiphen bromide. These compounds do not contain halogen substitution in a phenyl ring and are also seen as being insufficiently effective in controlling microorganisms associated with dental plaque. Other antiseptics which contain chlorine attached to a phenyl ring but are not generally used as oral antiseptics are hexachlorophene and triclocarban. Hexylresorcinol, a non-halogenated antiseptic, has been considered but is thought to be insufficiently effective against plaque forming organisms and in addition has a toxicity which is greater than desired for human use. There are many other antiseptics, but most have toxicities which are too high, especially for oral use.

Halogenated salicylanilides have been studied as possible antiseptic compounds, however, most have now been banned by the United States Food and Drug Administration from various over-the-counter products due to adverse effects which may result from the use. For example, tetrachlorosalicylanilide has been shown to produce allergic reactions in man, while certain other halogenated salicylanilides have been reported to produce photoallergic reactions.

It has been reported that certain tertiary butyl substituted salicylanilides are bactericides against the bacterium Staphylococcus aureus. To the time of the present invention it is not known what additional microorganisms might be affected by this compound and there is no indication that it might be effective against the traditionally difficult bacteria involved in dental plaques and associated diseases (Japanese Patent 75,129,738, Oct. 14, 1975).

U.S. Pat. No. 4,287,191 describes various 5-acylsalicylanides which are said to be effective antiseptics against a wide range of microorganisms, especially bacteria and the microorganisms prevalent in dental plaque. Though the 5-acylsalicylanides appears to show highly effective activity against several of the microorganisms associated with dental plaque, their reduced ability in clinical studies to inhibit the growth of Streptococcus mutans, a particularly resistant microorganism, has raised a question concerning their overall effectiveness.

There is therefore a need for an effective non-toxic antiseptic for general purpose use which may be, but is preferably not, halogenated with chlorine or bromine and there is definitely a need for a non-toxic antiseptic which is effective against the microorganisms associated with dental plaques, particularly S. mutans, and associated diseases.

BRIEF DESCRIPTION OF THE INVENTION

In accordance with the present invention there are provided novel compounds which may be, but are not necessarily, halogenated with chlorine or bromine and which are highly effective antiseptics with low toxicity in their preferred form. Very surprisingly, these compounds are highly effective against organisms associated with dental plaques, particularly S. mutans, various forms of caries, various periodontal diseases and other oral infections.

The compounds of this invention comprise certain 5-alkylsulfonylsalicylanilides and more particularly comprise the compounds encompassed by the following generic formula:

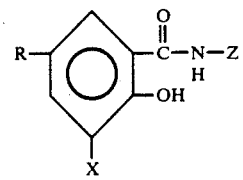

Wherein Z is a substituted phenyl ring of from 6 to 30 carbon atoms including substituents; R is a substituted or unsubstituted alkylsulfonyl group of from 1 to 20 carbon atoms including substituents; and, X is a radical selected from the group consisting of —CN, —NO₂, —H, halogen, lower alkyl or lower haloalkyl.

The preferred compounds of the invention have a partition coefficient greater than 4 and the substituted moieties in the phenyl ring of the Z group have a combined overall electron withdrawing effect on the phenyl ring of the Z group.

The above compounds and compositions containing them are effective antiseptics against a wide range of bacteria and the preferred compounds, surprisingly, are especially effective against a prevalent microorganism in dental plaque, *Streptococcus mutans*. In addition, the compounds of the invention are effective against many other organisms associated or not with periodontal diseases including *Actinomyces naeslundii*, *Actinomyces viscosus*, *Bacteroides asaccharolyticus*, *Bacteroides intermedius*, *Bacteroides gingivalis*, *Actinobacillus actinomycetemcomitons*, *Haemophilus segnis*, *Staphylococcus aureus*, *Staphylococcus epidermidis*, *Streptococcus pyogenes*, *Capnocytophaga ochracea*, *Treponema denticola*, *Fusobacterium nucleatum* and *Streptoccus sanguis*.

DETAILED DESCRIPTION OF THE INVENTION

As previously discussed, the present invention is concerned with certain antiseptic compounds and compositions and particularly certain 5-alkylsulfonyl derivatives of salicylanilides. These compounds all have at least some antiseptic properties and the preferred compounds have excellent antiseptic properties, especially against microorganisms associated with dental plaques and associated oral diseases. Furthermore, many of these compounds are characterized by having low toxicity to mammals. Additionally, the invention includes the method for controlling the growth of microorganisms by contacting the microorganisms with a compound of the invention for a sufficient time to kill or inhibit the growth or reproduction of the organism. The contact of the microorganism with the compound may be accomplished in either in vivo or in vitro environments.

The compounds of the invention comprise the compounds encompassed by the following generic formula:

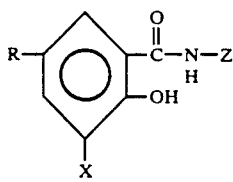

Wherein Z is a substituted phenyl ring of from 6 to 30 carbon atoms including substituents; R is a substituted or unsubstituted alkylsulfonyl group of from 1 to 20 carbon atoms including substituents; and, X is a radical selected from the group consisting of —CN, —NO₂, —H, halogen, lower alkyl or lower haloalkyl.

The preferred compounds of the invention have a partition coefficient greater than 4 and the substituted moieties in the phenyl ring of the Z group have a combined overall electron withdrawing effect on the phenyl ring of the Z group.

Partition coefficient of a composition as used herein is the $\log_{10} P$ where P is the ratio of the concentration of the composition in octanol to the concentration of the composition in water in a two phase octanol-water system. A partition coefficient of 4 therefore means that the ratio of the concentration of the composition in octanol to the concentration in water is $10^4$ or 10,000 to 1. The partition coefficient is a measure of the lipophylic character of the compound. The preferred compositions of the invention are lipophylic as indicated by a partition coefficient of greater than 4. The partition coefficient is however usually less than 10.

"Substituted" as used herein means that the organic composition or radical to which the term is applied is: at least one hydrogen in the compound or radical is replaced with a moiety (Y) containing one or more carbon, oxygen, sulfur, nitrogen or halogen atoms.

Moieties containing only carbon and hydrogen which may replace hydrogen as previously described include alkyl, alkenyl, alkynyl, alkyldienyl, cycloalkyl, phenyl, alkylphenyl, naphthyl, anthryl, phenanthryl, fluoryl, steroid groups, and combinations of these groups with each other and with polyvalent hydrocarbon groups such as alkylene, alkylidene and alkylidyne groups. Specific examples of such groups are: —CH₃, —CHCH₃CH₃. —(CH₂)hd 8CH₃, —CH₂—CH=CH₂. —CH=CH-CH=CH₂,

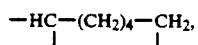

—ɸCH₃, —ɸCH₂ɸ, —ɸ, and —ɸ—ɸ.

Moieties containing oxygen which may replace hydrogen as previously described include hydroxy, acyl or keto, ether, epoxy, carboxy, and ester containing groups. Specific examples of such oxygen containing groups are: —CH₂OH,

—CH₂COOH,

—OCH₂CH₃, =O, —OH, —CH₂—O—CH₂CH₃, —CH₂—O—(CH₂)₂—OH,

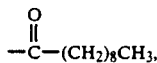

—CH₂CH₂COOH, —ɸOH, —ɸOCH₂CH₃, —ɸCH₂OH, —ɸOCH₂CH₃,

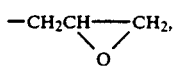

and —CH₂CH₂COOH.

Examples of moieties containing sulfur which may replace hydrogen are the sulfur containing acids and acid ester groups, thioether groups, mercapto groups and thioketo groups. Specific examples of such groups are: —SCH₂CH₃, —CH₂S(CH₂)₄CH₃, —SO₃CH₂CH₃, —SO₂CH₂CH₃, —CH₂COSH, —SH,

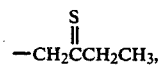

—SO₃H,

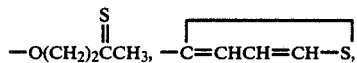

and =S.

Examples of moieties containing nitrogen which may replace hydrogen are amino groups' the nitro group, azo groups, ammonium groups, amide groups, azido groups, isocyanate groups, cyano groups and nitrile groups. Specific examples of such groups are: —NHCH₃, —NH₂, —NH₃+, —CH₂CONH₂, —CH₂CON₃, —CH₂CH₂CH=NOH, —CN, —CHCH₃CH₂NCO, —CH₂NCO.

—ϕN=NϕOH, and =N.

Examples of moieties containing halogen which may replace hydrogen are chloro, bromo, fluoro, iodo groups and any of the moieties previously described where a hydrogen or a pendant alkyl group is substituted by a halo group to form a stable substituted moiety. Specific examples of halogen containing moieties are: —(CH₂)₃COCl, —ϕCl, —CF₃, and —CH₂ϕBr.

It is understood that any of the above moieties can be substituted into each other in either a monovalent substitution or by loss of hydrogen in a polyvalent substitution to form another monovalent moiety which can replace hydrogen in the organic compound or radical. "Lower alkyl" as used herein means an alkyl group of from 1 to about 10 carbon atoms. "—ϕ" as used herein represents a phenyl ring.

A generic formula which includes many of the preferred compositions of the invention is:

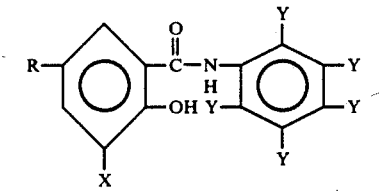

with R being an alkylsulfonyl radical of the formula

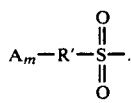

wherein —R'— is a saturated or unsaturated halogenated or unhalogenated alkyl group containing 1 to about 30 carbon atoms. Examples of preferred —R'— groups are: —(CH₂)₆—, —(CH₂)₇—, —(CH₂)₈—, —(CH₂)₉—, —(CH₂)₁₀—, —(CH₂)₁₁—(CH₂)₁₂— and —(CH₂)₁₃—. Other —R'— groups are —(CH₂)₆(CCl₂)—, —(CF₂)₆—, and (—CCl₂)₈—. It is apparent that the forgoing are only examples of possible —R'— groups.

A is independently at each occurrence —H, —OH, -halogen, lower alkoxy, lower alkyl, —SH, thioalkyl, phenyl, phenoxy, —NH₂, lower amino or lower acyl group. A is most preferably methyl (—CH₃) or —H. In general when A contains oxygen or another group or element which tends to increase the hydrophylic nature of the R group, additional lipophylic groups or elements must be present so that the overall hydrophylic-lipophylic balance of the R group decidedly favors solubility in fats or oils. As used herein lipophylic means the tendency to be attracted to fats or oils and as is well known hydrophylic means to be attracted to water. The R group should in fact be sufficiently lipophylic to give an overall lipophylic character to the composition, i.e. a partition coefficient greater than 4.

In the generic description of the invention, m is an integer of from 1 through 3 and in the preferred embodiments of the invention is usually 1 since pendant groups from the —R'— moiety usually do not add greatly to the antimicrobial character of the compounds and even if they do the same pendant groups often can increase toxicity to mammals. In this regard it is pointed out that the surprising effectiveness of the instant claimed compounds to *S. mutans* is believed to result from the attachment of the sulfonyl group to the phenyl of the salacylate moiety and subsequent enhancement by the —R'— moiety. Pendant groups which are hydrophylic, in particular, have been found to reduce antimicrobial activity unless more lipophylic groups are added to the R moiety to offset them.

Y is independently at each occurrence —H, lower alkyl, halogenated lower alkyl, —NO₂, —CN, -halogen, lower acyl, —SO₂R", or —SO₃R" where R" is lower alkyl or halogenated lower alkyl, provided that at least one of Y is not H or lower alkyl. Generally Y is not chlorine or bromine when applied to humans due to the increased toxicity or carcinogenicity often associated with halogenated phenyl rings. Halogen has however been found to sometimes even further increase antimicrobial activity and thus is nevertheless sometimes used especially when the compound is used only in in vitro environments. Halogen, especially fluorine, can be used with benefit and causes very little or no increase in toxicity when the halogen is attached to an aliphatic carbon atom instead of directly to the phenyl ring. An example of a very good Y group is —CF₃. In general all good Y groups are electron withdrawing groups and desirably are not strongly hydrophylic or water solubilizing groups. A particularly good Y group is —NO₂ especially when it is in the 4' position on the phenyl ring. Another very good Y group is —F. X is as previously described.

Examples of compounds especially suitable for use in accordance with the invention are those compounds wherein A is —H, m=1, Y is —NO₂ or —Br in the 4' position or —CF₃ in the 3', 4' or 5' positions. Examples of other compounds highly suitable for use in accordance with the invention are those compounds wherein m is 1 or 2, at least one A is not —H and Y is independently at each occurrence —H, -halogen, —NO₂, —CN, halogenated lower alkyl, —CHO, or lower acyl. R' may be cycloalkylene as previously discussed.

Examples of specific compounds in accordance with the invention are the compounds having the formula:

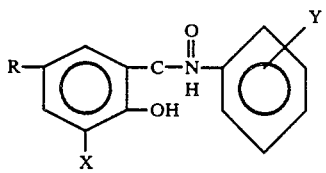

where R is

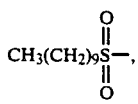

X is H— and Y is —NO$_2$, —Br or —CF$_3$ attached at the meta or para position;
where R is

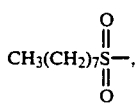

X is H— and Y is —NO$_2$, —Br or CF$_3$ attached at the meta or para position;
where R is

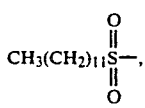

X is H— and Y is —NO$_2$, —Br or CF$_3$ attached at the meta or para position;
attached R is $$CH_3(CH_2)_{13}\overset{\overset{O}{\|}}{\underset{\underset{O}{\|}}{S}}-,$$

X is H— and Y is —NO$_2$, —Br or CF$_3$ attached at the meta or para position;
where R is

X is H— and Y is —Br or CF$_3$ attached at the para position or hydrogen;
where R is

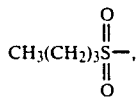

X is H— and Y is —CF$_3$, —Br or —NO$_2$ attached at the para position; and,
where R is

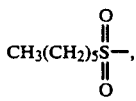

X is H— and Y is —CF$_3$. —Br or —NO$_2$ attached at the para position or hydrogen.

The method in accordance with the present invention for inhibiting the growth of microorganisms and especially bacterial organisms comprises contacting the organism for a sufficient time with a composition containing a sufficient concentration of a compound or mixture thereof of the invention, suitable compounds being those previously generically and specifically described. In general, the sufficient concentration of the compound is from about 0.01 to about 50.0 micrograms per milliliter of composition. Substantially higher concentrations may be used, however, even up to and exceeding as much as about 10% concentrations may be appropriate. The medium may be any appropriate solid, semi-solid or liquid. Examples of media upon which the composition may be used are organic tissue, dental surfaces, floors, walls, hardware and implements in general. The compounds may also be included in paints, textiles, leather, synthetic resins, foods, oral hygiene products, medicines and other ingestible substances. The compounds may be used in or on the media as antiseptics, disinfectants, antimicrobial medicines or preservatives. It is to be understood that the above sufficient concentrations are those required to be in actual contact with the microorganism and substantially higher concentrations may be required in antiseptic preparations when penetration through a substance is required in order to contact the microorganism with the composition of the invention. The sufficient time is the time required to inhibit the growth of the microorganism and may be the entire time of inhibition and when the microorganism is killed by the composition is usually from about 10 seconds to 30 minutes.

The compositions may be used as additives to dentifrices, soaps, deodorants and sterilizing solutions to enhance or provide antimicrobial properties to these products.

Microorganism, as used herein, includes any microorganism whose growth can be inhibited by the compositions of the invention. Such microorganisms include almost all bacteria and are also believed to include many fungi. It is also possible that some other protists and perhaps even some viruses are included.

In general the compounds in accordance with the invention are prepared by reacting a salicylic acid with a chlorosulfonic acid to form a 5-chlorosulfonylsalicylic acid. The 5-chlorosulfonylsalicylic acid is then reacted with an alkali metal sulfite to form 5-sulfinylsalicylic acid. The 5-sulfinylsalicylic acid is then reacted with an appropriate alkane such as a halogenated alkane to produce the 5-alkylsulfonylsalicylic acid. The 5-alkylsulfonylsalicylic acid then can be readily reacted with an appropriate substituted or unsubstituted aniline in the presence of a solvent to produce the compound of the invention. More specifically the synthesis of the compounds in accordance with the invention is believed to follow the following reaction scheme:

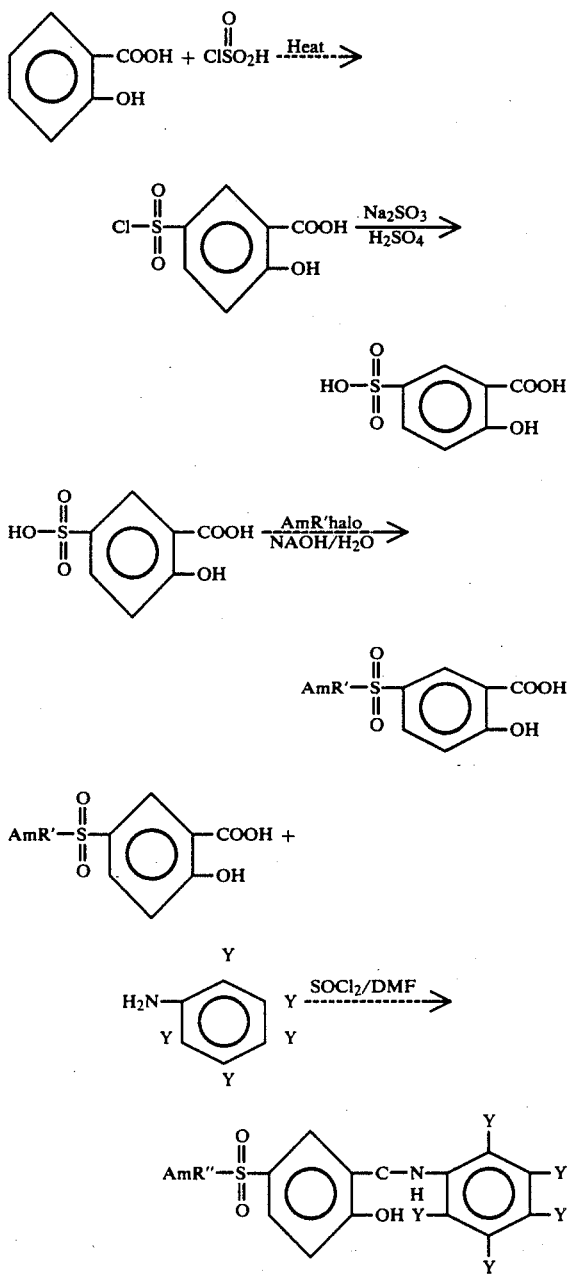

AmR' and Y are as previously described. An X group may be present in the original salicyclic acid reactant.

By the preferred procedure of the present invention, chlorosulfonic acid is reacted with salicylic acid to form the 5-chlorosulfonylsalicylic acid. The process typically comprises mixing cooled chlorosulfonic acid with the salicylic acid until the salicylic acid is dissolved and then heating the solution to form the 5-chlorosulfonylsalicylic acid. It should be understood however that various other reactive sulfonic acids can be used in the process of the invention including those which directly result in the formation of the 5-AmR' sulfonylsalicylic acid. The 5-chlorosulfonylsalicylic is then combined with a suitable base, we have found sodium sulfite in NaOH particularly suitable, and the mixture reacted with an acid (preferably $H_2SO_4$) to form the 5-sulfinylsalicylic acid. The sulfinyl radical is substituted with the desired alkyl (AmR') moiety by reacting with a compound having a suitable reactive site, such as halogenated alkane and treated with a base to provide the 5-alkylsu lfonylsalicylic acid. Reaction of the 5alkylsulfonylsalicylic acid with an appropriate substituted or unsubstituted aniline in the presence of a suitable solvent produce the compounds of the invention. Preferably, the 5-alkylsulfonylsalicylic acid is pretreated with a solution of thionyl chloride and dimethyl formamide by heating to a suitable temperature of between about 35° to 80° C. and maintaining the mixture at that temperature range for from a few minutes to several hours. The mixture is cooled and then treated with an appropriate substituted or unsubstituted aniline in the presence of a solvent for from 30 minutes to several hours to produce the compounds of the invention.

The following examples are provided to illustrate the invention and are not meant to provide limitation thereto.

EXAMPLES

EXAMPLE 1

Synthesis of 5-chlorosulfonylsalicylic acid

To 125 ml of chlorosulfonic acid in a round bottom flask, cooled with an ice bath, was slowly added 25 g. of salicylic acid with constant stirring. After all the salicylic acid was dissolved the cool mixture was heated in an oil bath, at 75° C. under constant stirring, for about 1 hour. The heated mixture was then carefully poured onto about 500 g. of crushed ice forming a white solid. The white solid was collected in a Buchner funnel and was recrystallized from $CH_2Cl_2$ to provide a 60% yield of a product having a melting point of 170°–172° C. and identified as 5-chlorosulfonylsalicylic acid.

EXAMPLE 2

Synthesis of 5-sulfinylsalicylic acid

The product of Example 1 (5 g.) was slowly added to a mixture of 20 g. of sodium sulfite in 100 ml of water, with the mixture being maintained basic by adding 20% NaOH:water solution as necessary. After all of the 5-chlorosulfonylsalicylic acid had been added, a solution of 20% $H_2SO_4$ in water was added until the pH of the mixture was less than 2. The resulting product was extracted (3×100 ml) with ether and the combined extracts were dried with anhydrous $MgSO_4$ and concentrated to provide an 85% yield of a product having a melting point of 150°–154° C. and identified as 5-sulfinylsalicylic acid.

EXAMPLE 3

Synthesis of 5-n-decylsulfonylsalicylic acid

Three grams of 5-sulfinylsalicylic acid were added dropwise, over a one hour period, to a refluxing solution containing 1.6 g. $Na_2CO_3$ in 50 ml of $CH_3OH$. Thereafter, 2.5 equivalents of 1-bromodecane was added, dropwise over a one hour period, to the refluxing mixture and refluxing was maintained for an additional 48 hours. The solvent was removed from the reaction mixture by rotary evaporation at reduced pressure and the resulting residue was redissolved in 50 ml of ethanol. Fifty ml of 10% aqueous NaOH solution was added to the ethanol residue solution and the mixture was refluxed for 24 hours. The mixture was cooled and acidified to a pH of 1 with a 20% aqueous HCl solution. The resulting product was extracted with ether (2×100), dried with MgSO4 and concentrated at reduced pressure to yield a solid product. The solid product was recrystallized in CCl4 providing a 70% yield of a product having a melting point of 98°–99° C. and identified as 5-n-decylsulfonylsalicylic acid.

In a similar manner, using 1-bromoctane, 1-bromododecane, 1-bromotetradecane, 1-bromohexane, 1-bromobutane and bromomethane produces the equivalent 5-n-octyl-, 5-n-dodecyl-, 5-n-tetradecyl-, 5-n-hexyl-, 5-n-butyl-, and 5-methyl-sulfonylsalicylic acids.

EXAMPLE 4

Synthesis of 5-n-decylsulfonyl-4'-nitro-salicylanilide (a) Thionyl chloride (8.7 m.moles, 0.4 ml) and 0.15 ml of dimethyl formamide were slowly added to a solution of 2.7 g. (7.9 m.moles) of 5-n-decylsulfonylsalicylic acid in 50 ml of toluene and the resulting mixture was heated at 50° C. for one hour. The mixture was then cooled and concentrated by rotary evaporation at reduced pressure to form a thick syrup. The syrupy mixture was subjected to 21 mm mercury pressure to remove remaining solvent and produce a dry residue product.

(b) The dry residue product of (a) was dissolved in 50 ml of toluene and 1.1 g. (7.9 m.moles) of p-nitro aniline was added. The resulting mixture was refluxed for two hours, then cooled and subjected to rotary evaporation and a reduced pressure until a dry residue remained. The residue was recrystallized from methanol three times and provided a 45% yield of a product having a melting point of 149V-150° and identified as 5-n-decyl-sulfonyl-4'-nitro-salicylanilide.

EXAMPLE 5

Synthesis of 5-n-decylsulfonyl-4'-trifluoromethylsalicylanilide

The dry residue product of Example 4(a) was dissolved in 50 ml of toluene and 1.3 g (7.9 m.moles) of p-trifluoro methyl aniline was added. The resulting mixture was refluxed for two hours then cooled and subjected to rotary evaporation at a reduced pressure until a dry residue remained. The residue was recrystallized from methanol and was identified as 5-n-decylsulfonyl-4'-trifluoromethyl-salicylanilide having a melting point of 155°–157° C.

EXAMPLE 6

Synthesis of 5-n-decylsulfonyl-3'-trifluoromethylsalicylanilide

The dry residue product of Example 4(a) was dissolved in 50 ml of toluene and 1.3 g. (7.9 m.moles) of m-trifluoro methyl aniline was added. The resulting mixture was refluxed for two hours, then cooled and subjected to rotary evaporation at a reduced pressure until a dry residue remained. The residue was recrystallized from methanol and was identified as 5-n-decylsulfonyl-3'-trifluoromethyl-salicylanilide having a melting point of 108°–109° C.

EXAMPLE 7

Synthesis of 5-n-dodecylsulfonyl-4'-bromo-salicylanilide

Three grams of 5-sulfinylsalicylic acid produced in accord with the process of Example 2 was added dropwise, over a one hour period, to a refluxing solution containing 1.6 grams of $Na_2CO_3$ in 50 ml of $CH_3OH$. Thereafter, 2.5 equivalents of 1-bromododecane was added, dropwise over a one-hour period, to the refluxing mixture and refluxing was maintained for an additional 48 hours. The solvent was removed from the reaction mixture by rotary evaporation at reduced pressure and the resulting residue was redissolved in 50 ml of ethanol. Fifty ml of 10% aqueous NaOH solution was added to the ethanol residue solution and the mixture was refluxed for 24 hours. The mixture was cooled and acidified to a pH of 1 with a 20% aqueous HCl solution. The resulting product was extracted with ether (2×100), dried with MgSO4 and concentrated at reduced pressure to yield a solid product. The solid product was recrystallized in CCl4 providing a 70% yield of a product having a melting point of 98° C.–99° C. and identified as 5-n-dodecylsulfonylsalicylic acid.

Thionyl chloride (8.7 m.moles, 0.4 ml) and 0.15 ml of dimethyl formamide were slowly added to a solution of 2.7 g. (7.9 m.moles) of 5-n-dodecylsulfonylsalicylic acid in 50 ml of toluene and the resulting mixture was heated at 50° for one hour. The mixture was then cooled and concentrated by rotary evaporation at reduced pressure to form a thick syrup. The syrupy mixture was subjected to 21 mm mercury pressure to remove remaining solvent and produce a dry residue product.

The dry residue product was dissolved in 50 ml of toluene and 1.2 g. (7.9 m.moles) of p-bromo aniline was added. The resulting mixture was refluxed for two hours, then cooled and subjected to rotary evaporation and a reduced pressure until a dry residue remained. The residue was recrystallized from methanol three times and provided a 45% yield of a product having a melting point of 162°–163° C. and identified as 5-n-dodecylsulfonyl-4'-bromo-salicylanilide.

EXAMPLE 8

Acute oral toxicity of 5-n-decylsulfonyl-4'-trifluoromethyl-salicylanilide

Twelve female white rats averaging 250–300 grams in weight were fasted overnight and divided into three groups of four animals each. In one group each animal received, by gavage tube, 4 ml of an aqueous solution of 1% methylcellulose, the drug delivery vehicle. This group was the control group. The remaining two groups received doses of 750 and 2500 mg/kg respectively of 5-n-decylsulfonyl-4'-trifluoromethyl-salicylanilide in 4-ml aqueous 1% methyl cellulose suspension.

Within the first week following this single dose only one animal died. This animal was from the control group and examination of the animal showed a punctured lung, thus this death can be attributed to trauma associated with administration.

On the eighth day, a second animal died, this time from the 2,500 mg/kg dose group. An autopsy was performed and the cause of death was attributed to a punctured thoracic cavity during administration of the drug. The remaining lived and gained weight.

From this experiment it can be concluded that the $LD_{50}$ for 5-n-decylsulfonyl-4'-trifluoromethyl-salicylanilide by the single dose oral route is greater than 2,500 mg/kg in Sprague-Dawley white rats.

EXAMPLE 9

Plaque growth inhibition

Various compositions prepared in accord with the above examples were tested in vitro for plaque inhibition in comparison with prior art compounds. The test used is set forth in detail in *Comparison of Antiplaque*

Agents Using an In Vitro Assay Reflecting Oral Conditions by R. T. Evans et al, Journal of Dental Research, June 1977.

In summary incisor teeth from bovine mandibles, obtained immediately after slaughter, are cut into 4×8 mm enamel slabs and sterilized in a 0.15M NaCl solution buffered at a pH of 7.5 with 0.02M sodium phosphate (PBS soln). Before use the slabs are coated with sterile saliva and then rinsed twice in sterile PBS. The slabs are then placed in small plastic petri dishes containing various concentrations of the compositions to be tested. The test solution used in accordance is a solution of the test compound in a mixture of 20% by volume of ethanol, 40% by volume of propylene glycol and 40% by volume of a pH 8 aqueous buffer solution containing mono and di sodium phosphates. The slabs are left in the solution of the test compound for two minutes and then rinsed in sterile PBS solution. After rinsing, each slab is placed in a 10×75 mm cotton stoppered glass culture tube containing 1 ml of sucrose-broth culture medium which is then innoculated with a 24 hour culture of the desired microorganism standardized to an optical density $(OD)_{540}$ of 0.75 for A. viscosus and S. mutans. 50 1 of the inoculation medium is used. A. viscosus is incubated under aerobic conditions and the S. mutans is incubated under anaerobic conditions (5% $CO_2$ and 95% $H_2$). After incubation for about 24 hours the non-adherent organisms are removed and the tube is rinsed twice with 0.5 ml of PBS and the washings combined with the nonadherent organisms.

The tooth slabs are then transferred to 1 ml of 0.1 N NaOH and 1 ml of 0.1N NaOH is also added to the glass culture tubes. The slabs and tubes are then sonically agitated, if necessary to suspend the adherent organisms. The optical density of each of the three fractions is then measured on a spectophotometer. The tests are repeated with varying concentrations of the compositions being tested until growth inhibition curves can be developed. The 50% growth inhibition dosages ($ID_{50}$) are then determined with a reliability of +or −80% or better. The compounds tested are samples (a)-(e) as follows: (a) tribromosalan; (b) 5-n-decanoyl-4'-nitrosalicylanilide; (c) 5-n-decylsulfonyl-4'-nitrosalicylanilide; (d) 5-n-decylsulfonyl-4'-trifluoromethyl-salicylanilide; and, (e) 5-n-decylsulfonyl-3'-trifluoromethyl-salicylanilide. The results are set forth in Table 1.

EXAMPLE 10

Tube dilution assay of bactericidal effects

Various compositions prepared in accord with the above examples were tested in vitro for minimal concentration to inhibit or kill organisms in comparison to prior art compounds. The test used is set forth in detail in *Manual of Clinical Microbiology*, third edition, pages 456-475 (Macro-Broth Dilution Method), 1980, American society for microbiology.

In the test procedure serial dilutions of the antimicrobic compound are innoculated with the organism to be inhibited and incubated. The minimum inhibitory concentration (MIC) is the lowest concentration of antimicrobic compound that is achieved without visible growth of the organism. The test method comprises preparing a stock solution of antimicrobic compound and diluting it in a Meuller-Hinton broth. A series of sterile 13 by 100 mm, cotton-plugged, test tubes are set out wherein 2 ml of the broth diluted antimicrobic solution (working solution) is added to the first tube and to each remaining tube is added 1.0 ml of non-antimicrobic containing broth. 1.0 ml of working solution from the first tube is transferred to the second tube and thoroughly mixed therewith. Thereafter, 1.0 ml of the mixed solution is transferred to the third tube and mixed with the process continuing through the dilution steps desired. The tubes are then incubated at 35° C. for 16 to 20 hours. The incubated tubes are inspected and a large cluster of growth or definite turbidity is considered evidence that the antimicrobic compound has failed to inhibit growth. Various antimicrobic compounds designated (a)-(i) were tested for minimum inhibitory concentration in accord with the above procedure. Compounds (a)-(e) correspond to compounds (a)-(e) of example 9. Compounds (f)-(i) are as follows: (f) 5-n-octylsulfonyl-4'-nitrosalicylanilide; (g) 5-n-decylsulfony-4'-bromosalicylanilide; (h) 5-n-hexylsulfonyl-4'-bromosalicylanilide; and, (i) 5-n-dodecylsulfonyl-4'-trifluoromethyl salicylanilide. The results are set forth in Table 2.

TABLE 1

| Compound | | A. viscosus | | S. mutans | |
|---|---|---|---|---|---|
| | | Total Growth $ID_{50}$ | Maximum % Inhibition | Total Growth $ID_{50}$ | Maximum % Inhibition |
| Tribromosalan | (a) | $8.8 \times 10^{-4}$ | 53% at 0.2% | $1.2 \times 10^{-7}$ | 46% at 0.2% |
| 5-n-decanoyl-4'-nitrosalicylanilide | (b) | $1.1 \times 10^{-4}$ | 90% at 0.2% | $2.3 \times 10^{-2}$ | 59% at 0.2% |
| 5-n-decylsulfonyl-4'-nitro-salicylanilide | (c) | $2.3 \times 10^{-4}$ | 93% at 0.2% | $1.9 \times 10^{-4}$ | 80% at 0.2% |
| 5-n-decylsulfonyl-4'-trifluoromethyl-salicylanilide | (d) | $0.9 \times 10^{-4}$ | 95% at 0.2% | $1.9 \times 10^{-3}$ | 76% at 0.2% |
| 5-n-decylsulfonyl-3'-trifluoromethyl-salicylanilide | (e) | $6.8 \times 10^{-4}$ | 83% at 0.1% | $2.2 \times 10^{-3}$ | 47% at 0.1% |

As can be seen from the forgoing table, compounds of the present invention, are as good as or better than the commercial compounds tested in overall inhibition of the growth of the microorganisms tested. The organisms tested are believed to represent the most prevalent microorganisms associated with dental plaque.

TABLE 2

| | Minimal Inhibitory Concentration (μg/ml) | | | | |
|---|---|---|---|---|---|
| Compound | S. Mutans | A. viscosus | S. aureus | S. pyogenes | S. epidermidis |
| (a) | 1.0 | 0.5 | 1.0 | 0.5 | 0.5 |
| (b) | 5.0 | 0.05 | 0.1 | 0.1 | 0.1 |
| (c) | 0.5 | 0.5 | 0.5 | 0.5 | 0.5 |
| (d) | 0.5 | 0.1 | 0.5 | 0.5 | 0.1 |
| (e) | 5.0 | 0.5 | 20.0 | 0.5 | 0.5 |
| (f) | 0.5 | 1.0 | 5.0 | 5.0 | 5.0 |
| (g) | 1.0 | 0.5 | 5.0 | 0.5 | 0.5 |
| (h) | — | 5.0 | 5.0 | 5.0 | 10.0 |

TABLE 2-continued

| Compound | Minimal Inhibitory Concentration (μg/ml) | | | | |
|---|---|---|---|---|---|
| | S. Mutans | A. viscosus | S. aureus | S. pyogenes | S. epidermidis |
| (i) | — | 0.05 | 0.5 | 0.5 | 0.1 |

An examination of Table 2 clearly shows that the compounds of the invention are as good as and better than those of the prior art in killing established dental plaque with a short contact time.

What is claimed is:

1. A compound of the formula:

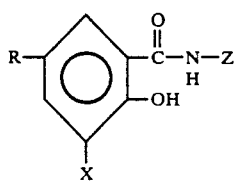

Where Z is a substituted phenyl ring of from 6 to 30 carbon atoms including substituents, R is a substituted or unsubstituted alkylsulfonyl group of from 1 to 20 carbon atoms including substituents and X is a radical selected from the group consisting of —CN, —NO₂, —H, halogen, lower alkyl or lower haloalkyl.

2. A compound of the formula:

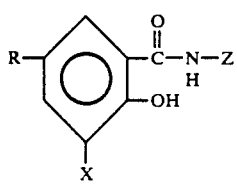

Where Z is a substituted phenyl ring of from 6 to 30 carbon atoms including substituents, R is a substituted or unsubstituted alkylsulfonyl group of from 1 to 20 carbon atoms including substituents and X is a radical selected from the group consisting of —CN, —NO₂, —H, halogen, lower alkyl or lower haloalkyl, said composition having a partition coefficient greater than 4 and the substituted moieties in the phenyl ring of the Z group having a combined overall electron withdrawing effect on the phenyl ring of the Z group.

3. A compound of the formula:

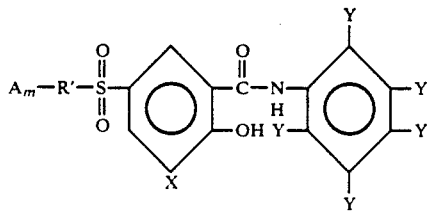

wherein —R'— is a saturated or unsaturated halogenated or unhalogenated alkyl group containing 1 through 20 carbon atoms; A is independently at each occurrence —H, —OH, lower alkoxy, —SH, thioalkyl, phenyl, phenoxy, —NH₂, lower amino or lower acyl group; m is an integer of 1 through 3; X is a radical selected from the group consisting of —CN, —NO₂, —H, halogen, lower alkyl or lower haloalkyl and Y is independently at each occurrence —H, lower alkyl, halogenated lower alkyl, —NO₂, —CN, -halogen, lower acyl, —SO₂R'', or —SO₃R'' where R'' is lower alkyl or halogenated lower alkyl, provided that at least one of Y is not H or lower alkyl and the compound has a partition coefficient of at least 4.

4. The compound of claim 3 wherein A is —H, m=1, X=H and at least one Y is —NO₂, —Br, —Cl, —F, or —CF₃

5. A compound of claim 1 of the formula:

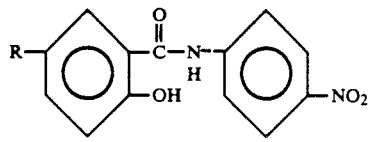

where R is CH₃(CH₂)₉

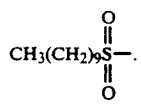

6. A compound of claim 1 of the formula:

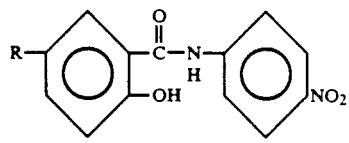

where R is

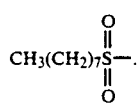

7. A compound of claim 1 of the formula:

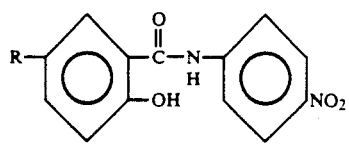

where R is

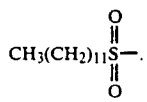

8. A compound of claim 1 of the formula:

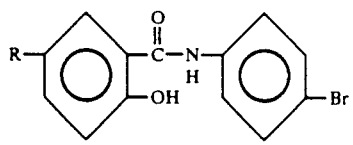

where R is

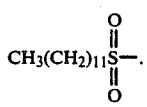
9. A compound of claim 1 of the formula:
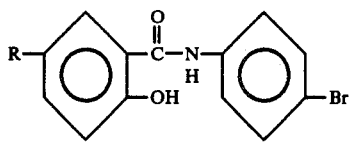
where R is
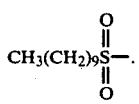
10. A compound of claim 1 of the formula:
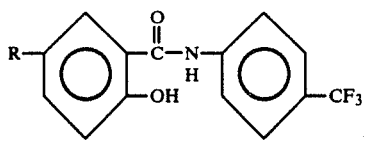
where R is
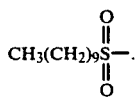
11. A compound of claim 1 of the formula:
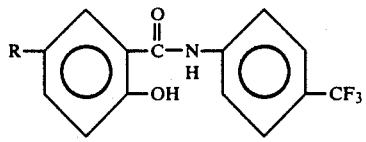
where R is
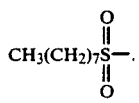
12. A compound of claim I of the formula:
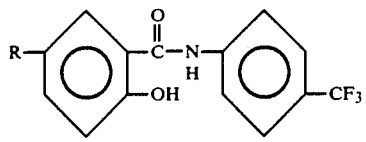
where R is
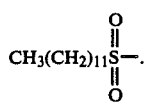
13. A compound of claim 1 of the formula:
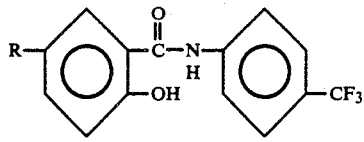
where R is
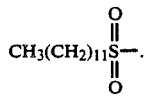
14. A compound of claim 1 of the formula:
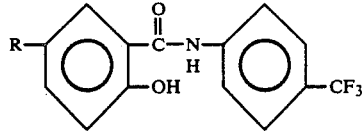
where R is
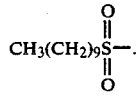
15. A compound of claim 1 of the formula:
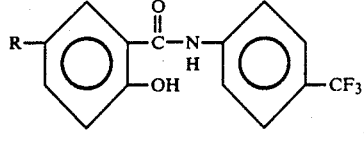
where R is
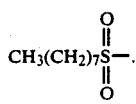
16. A compound of claim 1 of the formula:
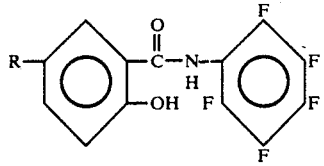
where R is 17. A compound of claim 1 of the formula:

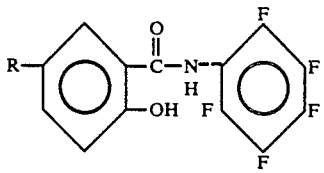

where R is

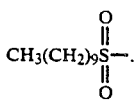

18. A compound of claim 1 of the formula:

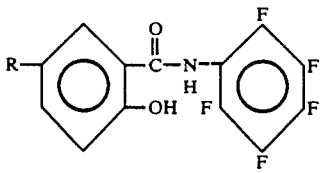

where R is

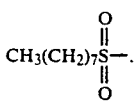

19. A compound of claim 1 of the formula:

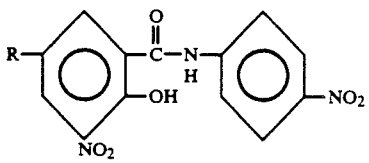

where R is

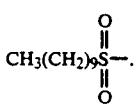

20. The compound of claim 3 wherein m is 1 or 2, at least one A is not —H and Y is independently at each occurrence —H, -halogen, —NO$_2$, —CN, halogenated lower alkyl, —CHO, or lower acyl.

21. A method for inhibiting the growth of microorganisms comprising contacting the organism with a compound of claim 1.

22. The method of claim 21 wherein the microorganism is a bacterial organism and the compound is applied in a concentration up to about 10% of compound per milliliter of medium containing the organism.

23. The method of claim 22 wherein the microorganism is a bacterial organism and the compound is applied to the microorganism, for a time from about 10 seconds to 30 minutes and the growth is inhibited by killing of the bacterial organism.

24. The method of claim 21 wherein the bacterial organism comprises *A. viscosus, A. naeslundii, S. mutans. B. intermedius, B. asaccharolyticus, S. sanguis, B. gingivalis, A. actinomycetemcomitans H. segnis, S. aureus, S. epidermidis, S. pyogenes, C. ochracea, T. denticola, F. nucleatum* or mixtures thereof.

25. A method for inhibiting the growth of microorganisms comprising contacting the organism with a compound of claim 2.

26. A method for inhibiting the growth of microorganisms comprising contacting the organism with a compound of claim 3.

* * * * *

UNITED STATES PATENT AND TRADEMARK OFFICE
CERTIFICATE OF CORRECTION

PATENT NO. : 4,939,132

DATED : July 3, 1990

INVENTOR(S) : Robert A. Coburn et al.

It is certified that error appears in the above-identified patent and that said Letters Patent is hereby corrected as shown below:

In Claim 5, line 3, delete "$CH_3(CH_2)_9$"

Signed and Sealed this

Nineteenth Day of February, 1991

Attest:

HARRY F. MANBECK, JR.

Attesting Officer

Commissioner of Patents and Trademarks